United States Patent [19]

Rosenthal et al.

[11] Patent Number: 5,436,455
[45] Date of Patent: Jul. 25, 1995

[54] NON-INVASIVE NEAR-INFRARED QUANTITATIVE MEASUREMENT INSTRUMENT

[75] Inventors: Robert D. Rosenthal, Gaithersburg, Md.; John J. Mastrototaro, Brentwood, Calif.; Joseph K. Frischmann, Indianapolis, Ind.; Reynaldo Quintana, Washington, D.C.

[73] Assignee: Futrex Inc., Gaithersburg, Md. ; a part interest

[21] Appl. No.: 106,758

[22] Filed: Aug. 16, 1993

Related U.S. Application Data

[63] Continuation-in-part of Ser. No. 813,739, Dec. 30, 1991, Pat. No. 5,237,178, which is a continuation-in-part of Ser. No. 565,302, Aug. 10, 1990, Pat. No. 5,077,476, which is a continuation-in-part of Ser. No. 544,580, Jun. 27, 1990, Pat. No. 5,086,229.

[51] Int. Cl.⁶ .......................................... G01N 33/50
[52] U.S. Cl. .................................................. 250/339.12
[58] Field of Search .................... 250/341, 339, 343; 256/39; 128/633

[56] References Cited

U.S. PATENT DOCUMENTS

| | | | |
|---|---|---|---|
| 4,882,492 | 11/1989 | Schlager | 250/341 |
| 4,971,062 | 11/1990 | Hasebe et al. | 128/664 |
| 5,237,178 | 8/1993 | Rosenthal et al. | 250/341 |

FOREIGN PATENT DOCUMENTS

| | | | |
|---|---|---|---|
| 3619442 | 12/1987 | Germany | 128/633 |

*Primary Examiner*—Paul M. Dzierzynski
*Assistant Examiner*—Richard Hanig
*Attorney, Agent, or Firm*—Rothwell, Figg, Ernst & Kurz

[57] ABSTRACT

An improved near-infrared quantitative analysis instrument is disclosed comprising a removable finger insert which facilitates properly aligning and fitting and individual user's finger into the optical system of the analysis instrument. The finger insert according to the present invention also prevents the analysis instrument's optical system from being damaged by foreign matter typically introduced by a user's finger. The finger insert can also be provided with filters which will enable the insert to be used to as an optical standard for the analysis instrument.

15 Claims, 6 Drawing Sheets

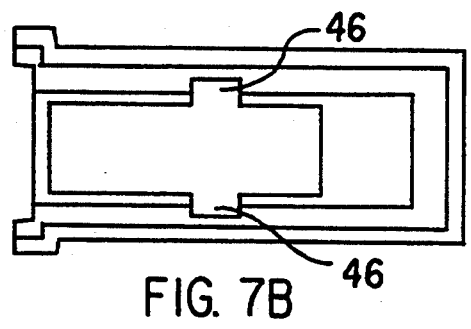
FIG. 7B
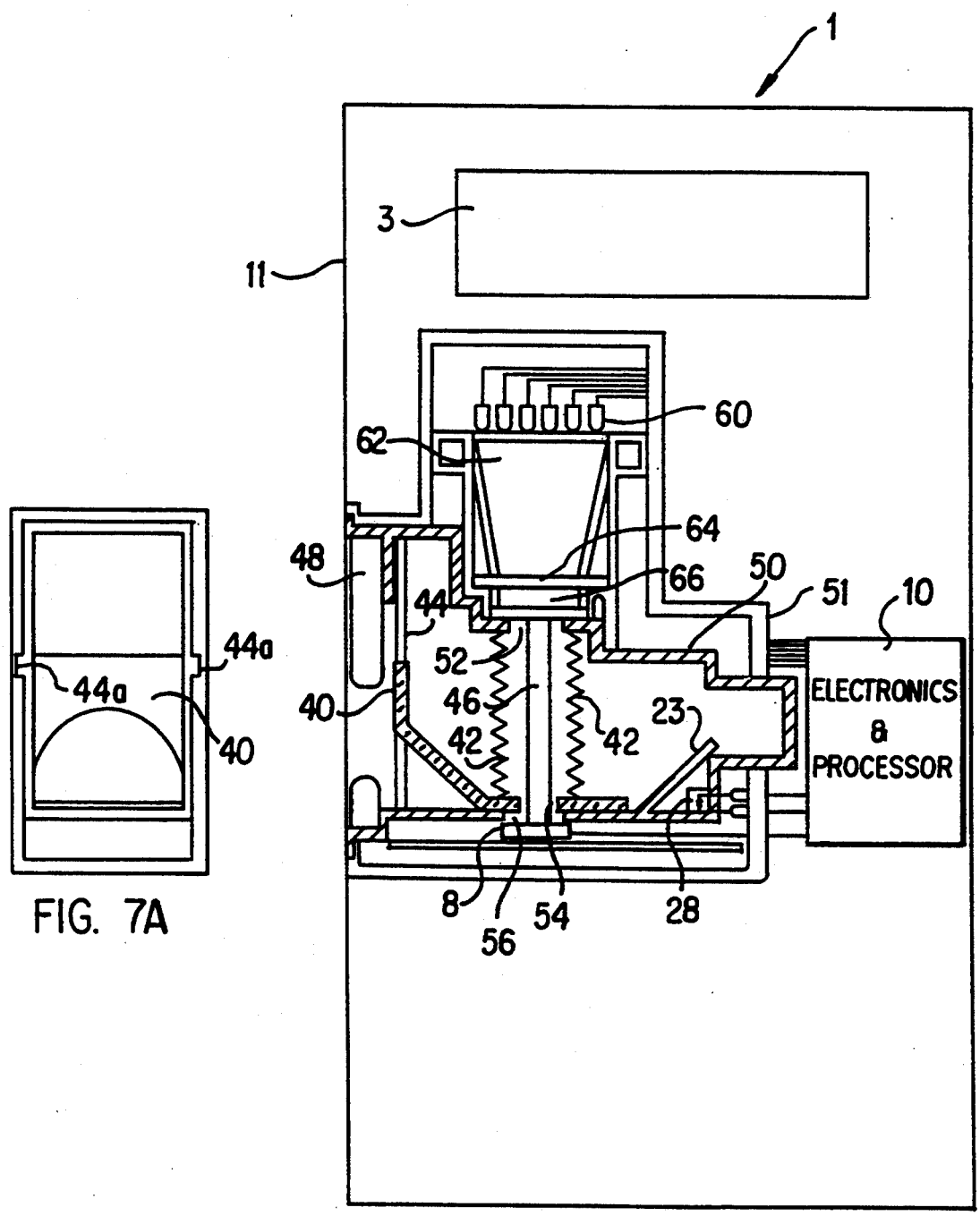
FIG. 7A
FIG. 7

NON-INVASIVE NEAR-INFRARED QUANTITATIVE MEASUREMENT INSTRUMENT

CROSS-REFERENCE TO RELATED APPLICATIONS

This application is a continuation-in-part of application Ser. No. 07/813,739, filed Dec. 30, 1991, which is a continuation-in-part of Ser. No. 07/565,302, filed Aug. 10, 1990, now U.S. Pat. 5,077,476, which is a continuation-in-part of application Ser. No. 07/544,580, filed Jun. 27, 1990, now U.S. Pat. No. 5,086,229.

BACKGROUND OF THE INVENTION

Field of the Invention

This invention relates to instruments for the noninvasive quantitative measurement of constituents in blood, such as blood glucose levels. Specifically, this invention relates to an improved analysis instrument utilizing a removable insert which facilitates positioning of an individual user's finger and improves the internal cleanliness of the instrument.

Description of the Background Art

Information concerning the chemical composition of blood is widely used to assess the health characteristics of both people and animals. For example, analysis of the glucose content of blood provides an indication of the current status of metabolism. Blood analysis, by the detection of above or below normal levels of various substances, also provides a direct indication of the presence of certain types of diseases and dysfunctions.

A current type of blood glucose analytical instrumentation is available for the specific purpose of determining blood glucose levels in people with diabetes. This technology uses a small blood sample from a finger poke which is placed on a chemically treated carrier and is inserted into a portable battery operated instrument. The instrument analyzes the blood sample and provides a blood glucose level reading in a short period of time.

A different class of blood glucose analytical instruments is the near-infrared quantitative analysis instrument which noninvasively measures blood glucose, such as the type described in U.S. Pat. No. 5,077,476 (Rosenthal). The noninvasive blood glucose measurement instrument analyzes near-infrared energy following interactance with venous or arterial blood, or transmission through a blood-containing body part. The instrument measures a change in light absorption that occurs, in part, due to the glucose content of the blood stream.

Non-invasive measurement instruments of this type have broad applications for the diabetic community. For example, people with diabetes have wide changes in their blood glucose content during the day which often require multiple measurements per day for good disease control. The ability to make these near-infrared blood glucose level measurements noninvasively means that more measurements will likely be made per day than would be made using the more painful blood drawing approach.

An example of a non-invasive measurement instrument is disclosed in the '229 patent wherein an individual user places the most distal portion of his or her finger within a "jaws" type arrangement. Near-infrared energy within the spectrum of interest is then impinged upon the surface of the finger and a detector is placed axially with the near-infrared beam on the opposite side of the finger to receive any nearinfrared energy emerging therefrom. A microprocessor receives the amplified signal from the detector and calculates the user's blood glucose level.

Another analysis instrument is disclosed in the '476 patent which comprises a chamber formed in the instrument housing into which a user inserts his or her finger. The user's finger must be correctly placed within the chamber so that proper exposure to the nearinfrared energy and detection can occur. In addition, this type of analysis instrument may measure the individual's skin temperature and use this measurement in calculating the blood analyte concentration. As a result, the individual's finger must properly be in contact with a skin temperature sensor to acquire the temperature measurement.

A possible limitation of the above-described instruments is that the instruments' optical systems can be damaged by the measurement of a person, especially children, having extremely dirty or wet fingers. Moreover, moisture and foreign matter can degrade optical transmission of the near-infrared energy thereby resulting in inaccurate blood glucose level measurements.

Another potential limitation associated with these instruments involves obtaining inaccurate blood glucose measurements resulting from a failure to properly and securely position a user's finger, which may vary widely in size, inside the instrument. This limitation is particularly applicable to taking measurements on a child's finger. Also, proper connection with a skin temperature sensor may not occur if an individual's finger is improperly positioned within the instrument's chamber.

Thus, there is a continuing need for an improved near-infrared analysis instrument having means for insuring the internal cleanliness of the instrument and means for more securely positioning an individual user's finger, which vary widely in size, inside the analytical instrument.

SUMMARY OF THE INVENTION

In accordance with the present invention, a nearinfrared quantitative analysis instrument for measuring a blood analyte comprises means for introducing nearinfrared energy into a body part of a subject, means for detecting near-infrared energy emerging from the subject and processing means for converting an electrical signal corresponding to the detected energy into a readout indicative of the blood analyte present in the blood of the subject. The analysis instrument is constructed having a housing means for housing at least the introducing means and the detecting means and a chamber means for permitting the body part to be exposed to the near-infrared energy. Also, an insert means is utilized for receiving the subject's body part and accurately placing the body part within the chamber means of the analysis instrument. The insert means removably engages the housing means and is aligned with the analysis instrument's optical system.

In accordance with another aspect of the invention, the insert means is semi-permanently and removably mounted into the chamber means of the analysis instrument. Thus, the individual user's body part is placed into the insert means which is already mounted outside the instrument's chamber. Utilizing the insert means according to the present invention will protect the instrument's cleanliness and assure proper positioning of body parts for different sized patients, i.e. child, average adult or large adult.

BRIEF DESCRIPTION OF THE DRAWINGS

FIG. 7 illustrates a noninvasive near-infrared glucose measurement instrument according to a third embodiment of the present invention;

FIG. 7A illustrates a front view of the finger insert mechanism of FIG. 7;

FIG. 7B illustrates a top view of the finger insert mechanism of FIG. 7;

DETAILED DESCRIPTION OF THE PREFERRED EMBODIMENTS

According to one embodiment of the invention, near-infrared light energy at bandwidths centering on one or more wavelengths of interest is transmitted through a blood containing portion of the body of a test subject. The near-infrared energy emerges from the test subject, generally opposite from the nearinfrared source, and is detected by a detector. Following amplification of the detector generated signal, the amplified output is processed into an output signal indicating the amount of blood analyte, such as blood glucose level, in the subject's blood.

Figure 1:
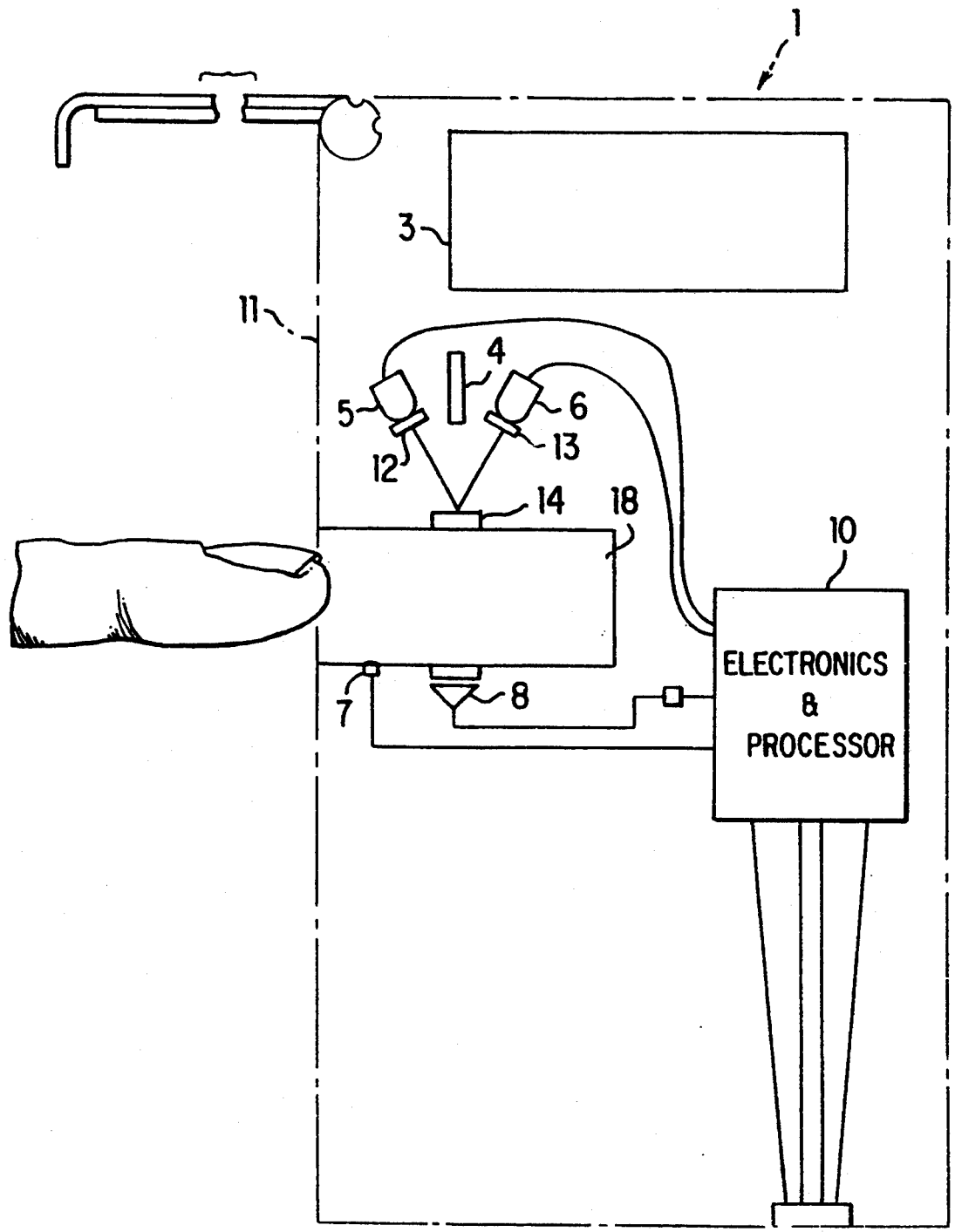
FIG. 1 illustrates a non-invasive glucose measurement instrument according to one embodiment of the present invention.

FIG. 1 illustrates a noninvasive near-infrared quantitative analysis instrument 1 which is designed to measure a blood analyte using near-infrared transmission through a test subject's body part, such as a finger. The analytical instrument 1 contains an introducing means including at least one near-infrared energy source for introducing near-infrared energy into the test subject's finger. In one embodiment of the present invention, the introducing means comprises up to six or more near-infrared point sources (nearinfrared emitting diodes or "IREDs"). IREDs 5 and 6 are shown for illustrative purposes in FIG. 1. In a preferred embodiment, the IREDs emit energy in the range of approximately 600 nanometers to approximately 1100 nanometers.

The analytical instrument also utilizes detector 8 for detecting near-infrared energy emerging from the test subject's body part. Detector 8 is electrically connected to data processing means 10 which, according to its programming, processes the signal produced by the detector 8 into a signal indicative of the quantity of blood analyte present in the test subject's blood, which is displayed on display 3. The analytical instrument 1 calculates the quantity of blood analyte present in the test subject's blood substantially as disclosed in U.S. Pat. No. 5,077,476, incorporated herein by reference.

Illustrative IREDs 5 and 6 are separated by light baffle 4 and are positioned so that the near-infrared energy is directed through window 14, which may be light scattering, and onto the test subject's skin. Window 14, however, is an optional component and is provided as a preferred embodiment. Optical filters, illustrated at 12 and 13, are positioned between each IRED and the window 14 for filtering the near-infrared light, thereby optimizing the band of near-infrared light striking the subject.

As illustrated in FIG. 1, the IREDs 5 and 6, detector 8 and processing means 10 are contained in a housing means which, preferably, is a light-weight hand-held housing unit 11. Housing means 11 further comprises a chamber means 18 for enabling the individual user's body part to be exposed to the near-infrared energy. The IREDs 5 and 6 and the detector 8 are positioned about the chamber means 18 forming an optical axis. During operation, the IREDs expose the subject's body part with near-infrared energy and detector 8 detects any energy emerging therefrom. Also, temperature sensor 7 is positioned about chamber means 18 such that it senses the user's skin temperature and produces a signal representative thereof. In one embodiment, temperature sensor 7 comes into actual contact with the user's skin. The measured skin temperature signal is input into the processing unit 10 which may be used in the calculation of the individual's blood glucose level.

However, as discussed above, potential errors in blood analyte concentration measurements may be caused by improper positioning of an individual's body part or by foreign matter degrading optical transmission.

Figure 2:
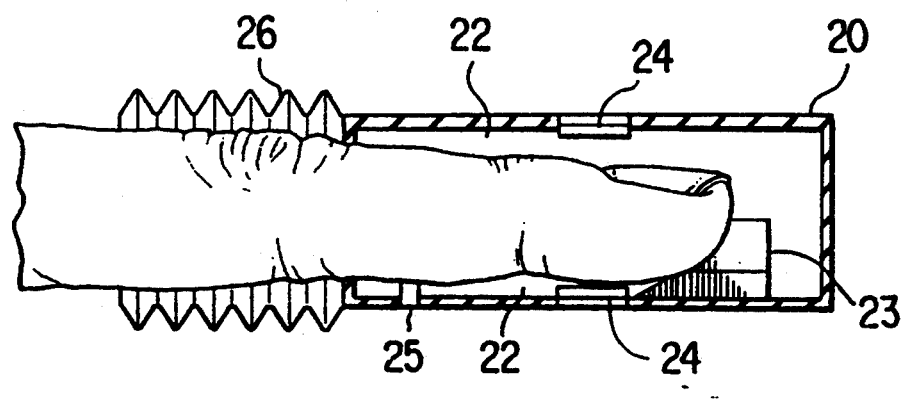
FIG. 2 is a cross-sectional view of the insert means according to one embodiment of the present invention.

Thus, in accordance with an important aspect of the present invention, FIG. 2 illustrates an insert means 20 for properly positioning an individual's body part inside the analysis instrument 1. In one embodiment, insert means 20 receives the test subject's body part, e.g. a finger, which are both then inserted into the chamber means 18 of the analysis instrument 1. As shown in FIG. 2, the insert means 20 comprises means for securely holding the individual's finger in place which insures its proper positioning within the analysis instrument's optical axis. The means for securely holding the individual's finger can be any suitable structure, such as foam rubber lining 22 or the like. Insert means 20 also includes a finger stop 23 which additionally facilitates finger positioning.

To enable the blood analyte measurements, insert means 20 includes a window means through which the near-infrared energy emitted from the IREDs 5 and 6 can impinge upon the test subject's finger and be detected by the detector 8. In one embodiment, the window means comprises first and second open portions in the insert means which are positioned to permit the near-infrared energy to be transmitted from the IREDs to the detector. In a preferred embodiment, the window means comprises portals 24 made of a material transparent to near-infrared energy, such as polystyrene, as shown in FIG. 2. The near-infrared openings can also be a ring-shaped structure formed around the insert means, or can be any other structure suitable for enabling the nearinfrared energy to be transmitted therethrough. Except for the near-infrared transmission openings, the insert means is preferably formed of an opaque material, such as PVC, which will protect against interference caused by external light.

Insert means 20 further comprises a conduction means 25 for conducting the heat from the individual's finger to the temperature sensor 7. Upon proper insertion, the conduction means 25 and the temperature sensor 7 will be in physical contact which will permit acquisition and utilization of the temperature signal by the processor 10. The conductor means 25 can be made of any suitable material such as brass.

Figure 3A:
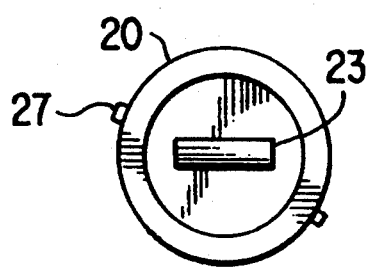
FIGS. 3A and 3B are each an end view of an insert means and illustrate the constant diameter and variable inner diameter of the insert means.
Figure 3B:
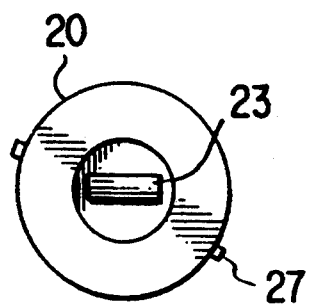

As described above, the insert means enables the proper positioning of user's fingers which may vary widely in size. This is accomplished by constructing the insert means with a constant outer diameter and by providing an inner diameter dimensioned to accommodate fingers of varying sizes, as illustrated by FIGS. 3A and 3B. Furthermore, constructing the insert means with a constant outside diameter and a choice of inside diameters, depending on finger size, will allow significant cost savings in the design of the analytical instrument. Other types of near-infrared analytical instruments have attempted to accommodate different finger sizes by loading a finger retainer, including a portion of the system optics, against the user's finger. Providing an insert with a constant outside diameter, however, will eliminate the need for movable optics.

In another aspect of a preferred embodiment, light shielding means for blocking out unwanted impinging sunlight, or any other type of optical radiation, is provided. If the near-infrared measurements are made in bright sunlight, the finger acts as a "fiber optic" equivalent and transmits light to the most distal portion where the glucose measurement is taken. To avoid this problem, the light shielding means is provided which can be any suitable structure for preventing stray light from interfering with blood glucose level measurements. For example, FIG. 2 shows an optically opaque bellows arrangement 26 attached to the insert means 20 and covering the finger portion which is external to the instrument. The light shielding means could be connected to the instrument housing as well. The bellows arrangement 26 can improve measurement accuracy by blocking out impinging sunlight or any other type of optical radiation.

Figure 4:
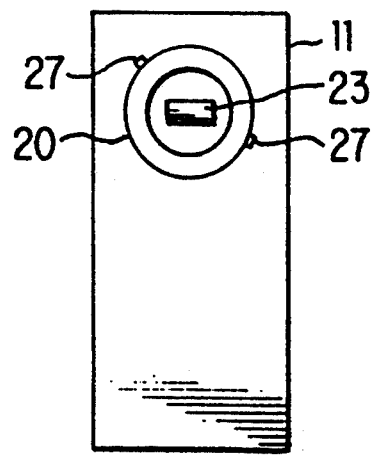
FIG. 4 is an end view of the analysis instrument having an insert means positioned inside its chamber and illustrates the channel means for properly positioning the insert means therein.

Properly using the insert means 20 with the analytical instrument 1 according to a first embodiment of the present invention will be described hereinafter. The individual user slides his or her body part to be measured, e.g. finger, into the insert means 20. The individual's finger will be securely positioned within the insert means by lining 22 and finger stop 23. After the finger is positioned within the insert, the insert is aligned and entered into the chamber means 18. As shown in FIGS. 3A, 3B and FIG. 4, alignment rails 27 are provided on the insert means to insure that it is properly inserted within the chamber 18. Thus, the insert means 20 enables the individual's finger to be securely fit and properly aligned within the analytical instrument. Blood analyte concentration measurements can then be performed as described above.

Figure 5:
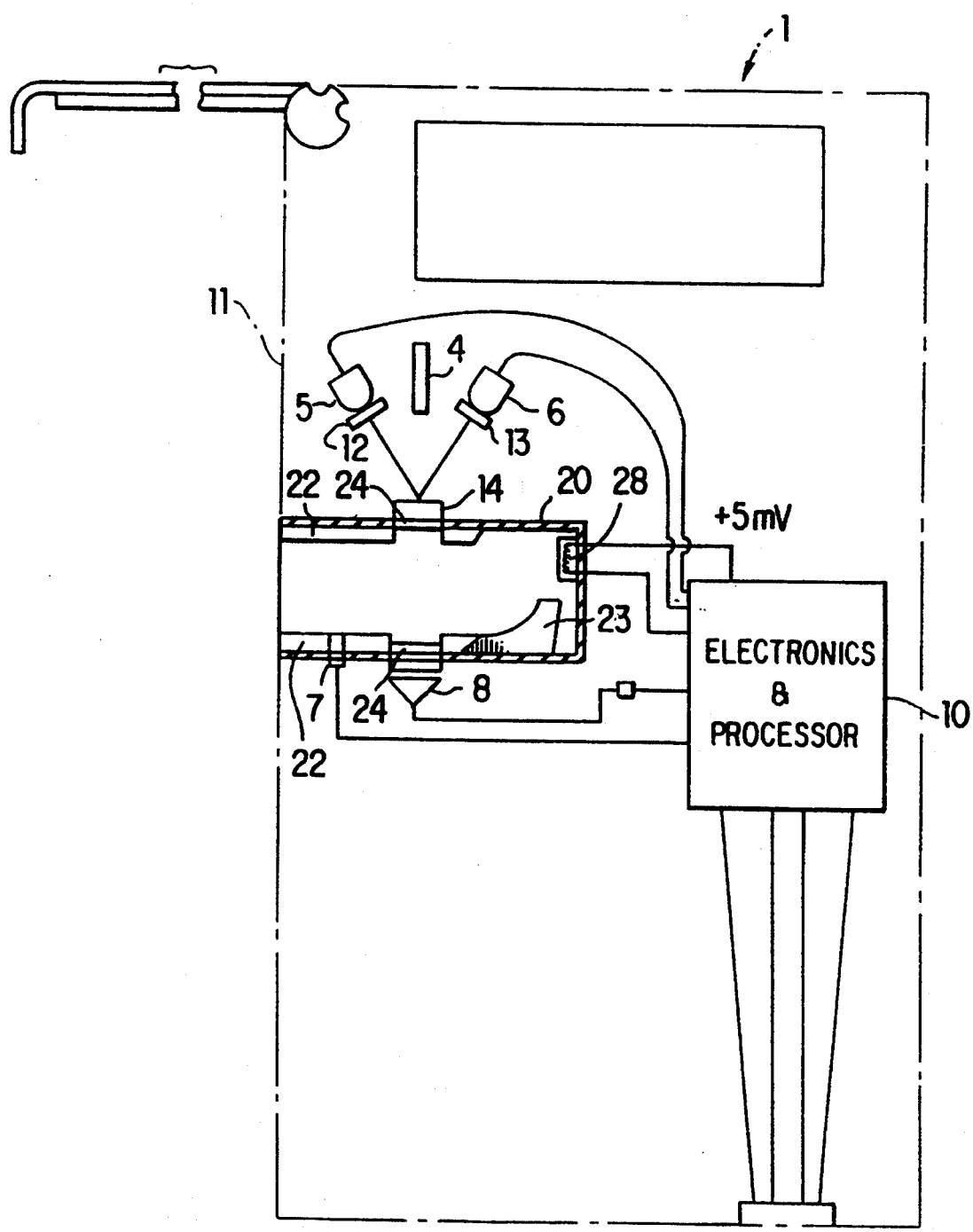
FIG. 5 illustrates a noninvasive near-infrared glucose measurement instrument according to a second embodiment of the present invention.

According to a second embodiment of the present invention, the insert means 20 is initially installed into chamber 18 of the analytical instrument 1 before receiving the user's finger, as illustrated in FIG. 5. Using this approach, the individual user's finger is placed into the insert means which is already in the instrument. This construction is advantageous in that the insert means is semi-permanently, removably, engaged by the instrument and is not a "loose piece" which can be lost. Also, the optical path for empty chamber measurement and for the finger measurement is consistent; both contain the insert.

Over a period of time, the insert means may become dirty, damaged or worn out due to multiple finger insertions. Thus, in accordance with another aspect of the invention, the analytical instrument is provided with a protection means for preventing the insert means from being used if it has been damaged or is otherwise unable to permit accurate blood glucose measurements. In one embodiment, the insert means 20 is provided with a safety device which informs the user to replace the insert after a predetermined number of days or uses. For example, the insert means shown in FIG. 5 is provided with a safety device 28 including means for completing an electrical circuit which enables the instrument to make blood glucose measurements. The means for completing the electrical circuit can be any suitable means known in the art. For example, safety device 28 comprises a filament which forms part of a circuit between a voltage source and processor 10. Voltage is applied to the filament while the instrument is taking blood glucose measurements. After the filament is expended, the time for which is selected to coincide with the desired useful life of the insert means, the instrument will be inactivated and will no longer perform measurements.

The processor 10 can perform the inactivation in any suitable way. For example, the signal from the filament can be to one input of an AND gate while the other AND gate input is from the instrument ON/OFF signal. After the instrument becomes inactivated, the individual user will then have to replace the insert means before additional blood glucose measurements can be taken.

In a second embodiment, the protection means uses the analytical instrument's optical system to determine when the insert means must be replaced. The optical system makes an initial measurement when the insert is first placed into the chamber 18 which is then stored in the instrument's memory. This initial measurement is made with an empty insert, i.e. no finger would be in place at that time. Over a period of time, empty insert measurements are made and the values obtained are compared with the initial Log 1/T values. If significant changes from the initial value are detected, such as a Log 1/T value of approximately 0.1, then the analytical instrument will not perform any further measurements until the insert means has been replaced. The protection means will insure that the instrument user will change the insert means to insure its cleanliness and, thus, enable more accurate blood glucose measurements.

Figure 6:
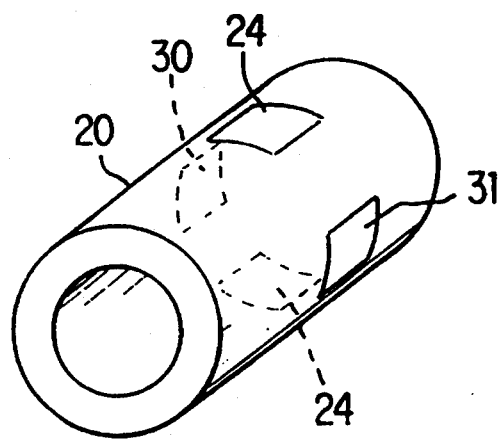
FIG. 6 illustrates an alternative embodiment of an insert means according to the present invention.

In still another aspect of the present invention, the insert means is used to provide an optical standard to test the instrument performance. The purpose of the optical standard is to satisfy the requirement that a measurement be made on an artificial substance to establish that the instrument is working properly. As shown in FIG. 6, insert means 20 is provided with a first optical filter 30 and a second optical filter 31, each located at 90 to the near-infrared transparent windows 24. Filters 30 and 31 can be made of any suitable material, such as plastic, ceramic or formed by vapor deposition on glass. The filters are arranged so that a pair of them can provide reading at two separate points in the spectrum. Thus, the optical standardization is performed by rotating the insert means such that optical filters 30 and 31 are in the instrument's optical axis and performing a first measurement reading. A second measurement is then taken after rotating the insert means 180 degrees. The two measurement points are slightly different because the light enters the filters in opposite ways, thus enabling the standard readings to be made. Finger measurements can be made by returning the insert to the original position.

In this embodiment, the insert means is constructed having the alignment rails only on a distal portion thereof. Also, the housing means comprises channel means for receiving the alignment rails which extend only partially along the length of the chamber means. When the insert means is positioned to perform blood glucose measurements, the alignment rails and the channel means are engaged and prevent the insert means from being rotated. However, the housing means comprises means for receiving the insert means an additional distance which frees the alignment rails from the channel means which permits the insert means to be rotated. The means for receiving the insert means an additional distance can be any suitable structure, such as spring loading the back wall of the chamber means.

A third embodiment of the invention will now be described with reference to FIGS. 7, 7A, 7B, 8, and 8A. Like elements of FIGS. 1–6 have been numbered with like reference numerals in FIGS. 7–8A, to avoid duplication of explanation. According to the third embodiment, an insert mechanism 50 is provided with a normally-closed spring-loaded sliding baffle 40, which is biased in the closed position by a pair of compression force springs 42. It is to be noted, however, that a single spring may be used equivalently instead of a pair of springs. The front of the measurement chamber 51 includes a diaphragm 48, preferably made of rubber material, which functions to tightly engage a test subject's finger and shield light from the chamber 51. So long as there is no finger in place, the sliding baffle 40 remains closed and there is no possibility of room light reaching the detector 8. Thus, a single insert may be provided which automatically adjusts according to the dimension of the finger being inserted into the instrument. Additionally, because the insert is normally closed, calibration measurements may be made more accurately by excluding external light, and the interior of the instrument may more easily be kept free of foreign matter.

In this embodiment, an array of IREDs 60 is provided in a housing block above the chamber 51. A Fresnel lens 62 may be provided at the output of the IREDs, with first and second diffusers 64 and 66 being provided at predetermined distances from lens 62 to increase the amount of light dispersion to achieve as uniform a distribution of light as possible for irradiating the test subject's finger. The insert 50 is provided with first and second apertures 52 and 56, and the sliding baffle 40 is provided with an aperture 54, to allow light from the IRED array to enter the chamber, irradiate the test subject's finger, and impinge upon the detector 8.

Figures 8, 8A:
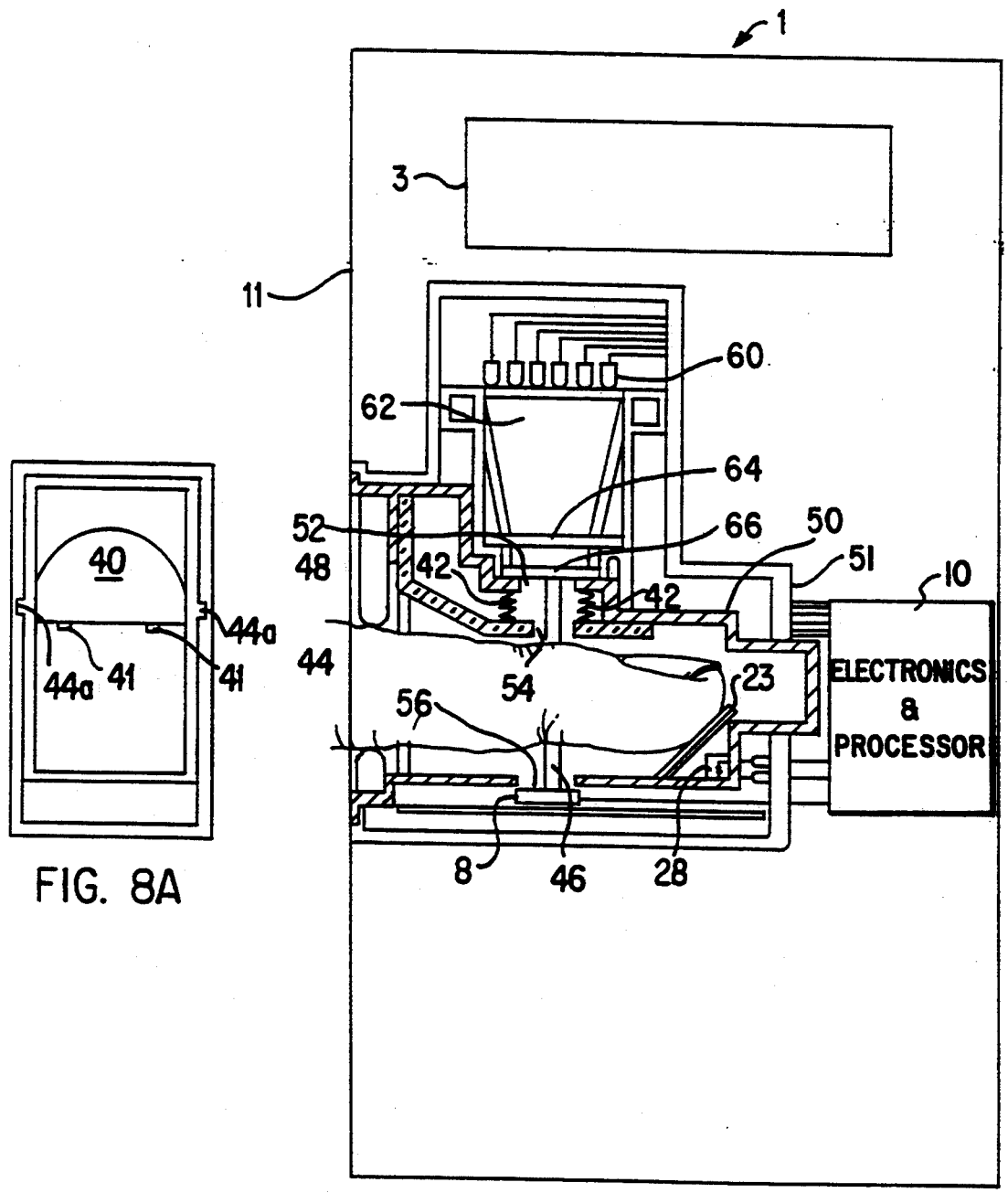
FIG. 8 illustrates the embodiment of FIG. 7 with a test subject's finger inserted into the instrument.
FIG. 8A illustrates a front view of the finger insert mechanism of FIG. 8.

As shown in FIG. 8, according to one embodiment, when a subject inserts their finger into the chamber, the sliding baffle 40 is caused to slide upward towards the top of insert 50, by application of force by the subject's finger on the springs 42. A constant force spring is ideally desired so that the same amount of resistance is presented to test subjects regardless of the size of their fingers, as opposed to a compression spring whose force varies linearly depending on the size of the finger. However, because of physical space constraints, a constant force spring cannot be used in the instrument. As an alternative, a compression spring with a low spring constant can be used to approximate a constant force spring. According to one embodiment, a force of 55g is used. The sliding baffle 40 is guided along vertical tracks 44 and 46, by engagement of tabs 44a in track 44 and corresponding tabs (not shown) engaging track 46. A pair of tabs 41 are provided on the bottom surface of the sliding baffle 40 for engagement with the bottom of insert 50.

In the ideal situation of perfect light collimation and diffusion, the position of aperture 54 of sliding baffle 40 relative to the light source and detector is irrelevant to a finger measurement. However, under non-ideal circumstances, the light pattern impinging upon the detector will change as a function of the position of the aperture 54. As a result, under these conditions the position of the aperture 54 must remain fixed during the finger reading and during the standard reading. Thus, whatever position the aperture 54 is in during finger measurement must be maintained during the standard reading. Under such conditions where the light source is not perfectly collimated and the emitted light is not perfectly diffused, the springs 42 may be omitted and replaced by another mechanism such as a small pressure sensitive motor or the like, or the sliding baffle 40 may be provided with external locking means to lock it in position after finger insertion so that a standard reading may be taken with the aperture 54 in a constant position.

Although the invention has been described in connection with preferred embodiments, it is not limited to them. Modifications within the scope of the following claims will be apparent to those skilled in the art.

What is claimed is:

1. A near-infrared quantitative analysis instrument for non-invasive measurement of a blood analyte present in a body part of a subject, said analysis instrument comprising:
   (a) introducing means including a near-infrared energy source for introducing near-infrared energy into blood present in a body part of a subject;
   (b) detecting means for detecting near-infrared energy emerging from the body part;
   (c) a housing means for housing at least said introducing means and said detecting means, said housing means comprising a chamber means for enabling said body part of said subject to be exposed to said near-infrared energy, said introducing means and said detecting means being positioned about said chamber means such that near-infrared energy emitted by said introducing means is receivable by said detecting means;
   (d) an insert means for receiving said body part of said subject, including means for semi-permanently engaging said chamber means, said insert means being semi-permanently engaged with said chamber means prior to receiving said body part of said subject; and
   (e) processing means for calculating an electrical signal from said detection means into a signal indicative of the quantity of said blood analyte present in the blood of the subject.

2. A near-infrared quantitative analysis instrument as set forth in claim 1, wherein said insert means comprises:
   a baffle means for covering, in a first normally-closed position, an external opening of said insert means through which said body part is received by said insert means;

means for causing said baffle means to withdraw to a second open position exposing said external opening of said insert means upon contact of said body part with said baffle means; and means for causing said baffle means to return to said first normally-closed position upon withdrawal of said body part from said insert means.

3. A near-infrared quantitative analysis instrument as set forth in claim 2, wherein said means for causing said baffle means to withdraw comprises at least one vertical track disposed in said insert means and engaging with said baffle means.

4. A near-infrared quantitative analysis instrument as set forth in claim 2, wherein said means for causing said baffle means to return to said first normally-closed position comprises at least one spring connected between said insert means and said baffle means and biasing said baffle means toward said normally-closed position.

5. A near-infrared quantitative analysis instrument as set forth in claim 3, wherein said means for causing said baffle means to return to said first normally-closed position comprises at least one spring connected between said insert means and said baffle means and biasing said baffle means toward said normally-closed position.

6. A near-infrared quantitative analysis instrument as set forth in claim 2, further comprising diaphragm means disposed around said external opening for engaging said body part when inserted into said insert means.

7. A near-infrared quantitative analysis instrument as set forth in claim 1, further including a lens disposed in said chamber means for focusing near-infrared energy from said energy source.

8. A near-infrared quantitative analysis instrument as set forth in claim 7, further including at least one diffuser means disposed in said chamber means for diffusing near-infrared energy passing through said lens.

9. A near-infrared quantitative analysis instrument for non-invasive measurement of a blood analyte present in a body part of a subject, said analysis instrument comprising:

(a) introducing means including a near-infrared energy source for introducing near-infrared energy into blood present in a body part of a subject;

(b) detecting means for detecting near-infrared energy emerging from the body part;

(c) chamber means for enabling said body part of said subject to be exposed to said near-infrared energy, said introducing means and said detecting means being positioned about said chamber means such that near-infrared energy emitted by said introducing means is receivable by said detecting means;

(d) an insert means, located within said chamber means, for receiving said body part of said subject, including a baffle means for covering, in a first normally-closed position, an external opening of said insert means through which said body part is received by said insert means, means for causing said baffle means to withdraw to a second open position exposing said external opening of said insert means upon contact of said body part with said baffle means, and means for causing said baffle means to return to said first normally-closed position upon withdrawal of said body part from said insert means; and (e) processing means for calculating an electrical signal from said detection means into a signal indicative of the quantity of said blood analyte present in the blood of the subject.

10. A near-infrared quantitative analysis instrument as set forth in claim 9, wherein said means for causing said baffle means to withdraw comprises at least one vertical track disposed in said insert means and engaging with said baffle means.

11. A near-infrared quantitative analysis instrument as set forth in claim 9, wherein said means for causing said baffle means to return to said first normally-closed position comprises at least one spring connected between said insert means and said baffle means and biasing said baffle means toward said normally-closed position.

12. A near-infrared quantitative analysis instrument as set forth in claim 10, wherein said means for causing said baffle means to return to said first normally-closed position comprises at least one spring connected between said insert means and said baffle means and biasing said baffle means toward said normally-closed position.

13. A near-infrared quantitative analysis instrument as set forth in claim 9, further comprising diaphragm means disposed around said external opening for engaging said body part when inserted into said insert means.

14. A near-infrared quantitative analysis instrument as set forth in claim 9, further including a lens disposed in said chamber means for focusing nearinfrared energy from said energy source.

15. A near-infrared quantitative analysis instrument as set forth in claim 14, further including at least one diffuser means disposed in said chamber means for diffusing near-infrared energy passing through said lens.

* * * * *